United States Patent [19]

Paglione et al.

[11] Patent Number: 4,632,128
[45] Date of Patent: Dec. 30, 1986

[54] ANTENNA APPARATUS FOR SCANNING HYPERTHERMIA

[75] Inventors: Robert W. Paglione; Oakley M. Woodward, both of Mercer County, N.J.

[73] Assignee: RCA Corporation, Princeton, N.J.

[21] Appl. No.: 745,690

[22] Filed: Jun. 17, 1985

[51] Int. Cl.⁴ .................................................. A61N 5/00
[52] U.S. Cl. .............................. 128/804; 219/10.55 R; 219/10.55 F; 374/121
[58] Field of Search ................ 128/804, 399, 736, 783, 128/422; 374/121, 122, 124; 343/720, 351; 219/10.55 R, 10.55 F

[56] References Cited

U.S. PATENT DOCUMENTS

| | | | |
|---|---|---|---|
| 2,549,399 | 4/1951 | Tawney | 128/804 |
| 3,457,924 | 7/1969 | Kendall | 128/804 |
| 3,800,802 | 4/1974 | Berry et al. | 128/422 |
| 3,924,196 | 12/1975 | Takahashi | 328/253 |
| 3,978,864 | 9/1976 | Smith et al. | 128/804 |
| 4,228,809 | 10/1985 | Paglione | 128/804 |
| 4,230,129 | 10/1980 | LeVeen | 128/804 |
| 4,271,848 | 6/1981 | Turner et al. | 128/804 |
| 4,341,227 | 7/1982 | Turner | 128/804 |
| 4,346,716 | 8/1982 | Carr | 128/653 |
| 4,397,314 | 8/1983 | Vaguine | 128/399 |
| 4,434,341 | 2/1984 | Busby | 219/10.55 |
| 4,448,198 | 5/1984 | Turner | 128/422 |
| 4,471,787 | 9/1984 | Bentall | 128/804 |

FOREIGN PATENT DOCUMENTS

| | | | |
|---|---|---|---|
| 3048682 | 9/1981 | Fed. Rep. of Germany | 128/804 |
| 0203686 | 11/1983 | Fed. Rep. of Germany | 128/804 |
| 1045546 | 10/1966 | United Kingdom | 128/804 |

Primary Examiner—Lee S. Cohen
Attorney, Agent, or Firm—Joseph S. Tripoli; Robert L. Troike; William H. Meise

[57] ABSTRACT

An arrangement for heating includes an antenna which has at least one convolution of conductor centered on an axis. The antenna is adapted for receiving electrical power for heating a surface. A noncontacting temperature sensor is centered on the axis of the antenna with its field of view directed along the axis.

14 Claims, 22 Drawing Figures

ANTENNA APPARATUS FOR SCANNING HYPERTHERMIA

BACKGROUND OF INVENTION

This invention relates to hyperthermia therapy in which the temperature of living tissue is increased for therapeutic purposes, and particularly to antenna apparatus for microwave hyperthermia treatment.

Hyperthermia treatments have for many years been used for treatment of cancers. It is known that raising of the temperature of cells to above about 43° to 45° C. for sufficient time causes necrosis, and temperatures below about 41.50 generally do not affect cells. Some types of malignant cells reportedly can be destroyed by raising their temperatures to levels slightly below those injurious to most normal cells. One of the techniques which has been used for hyperthermia is heating of the blood of a patient by an external apparatus, thereby raising the temperature of the entire body or a portion thereof to the therapeutic temperature. This procedure risks substantial injury to the patient if temperature is not carefully controlled, and may fail to raise the temperature of the malignant cells sufficiently for destruction. Any malignant cells which remain undestroyed may cause a recurrence of the tumor, growth or malignancy (hereinafter tumor).

Some surface tumors may be successfully treated by application of surface heat from a heated object. Deeply located tumors, however, are difficult to heat to therapeutic temperatures without destruction of the overlying tissue.

Another hyperthermia technique uses electromagnetic radiation to heat tissue. The electromagnetic radiation is often in the form of radio frequency (RF) or microwave radiation because of the ease of generating, controlling and directing microwaves, and also because of the absorption characteristics of tissue at microwave frequencies. At the current state of the art, microwave hyperthermia is usually at frequencies in the range of 10 MHz to 6 GHz. Microwave hyperthermia when applied to tissue containing a tumor generates heat within the tissue which raises the temperature of the tissue generally. It has been found that tumors tend to have a limited blood supply by comparison with healthy tissue. Thus, the circulation of blood through a tumor is low by comparison with circulation through healthy tissue. At any microwave power density, the tumor will usually be hotter than the surrounding healthy tissue because the more ample flow of blood in the healthy tissue provides cooling of the healthy tissue. Thus the tumor may be heated by microwave hyperthermia to a therapeutic temperature without significant effect on surrounding healthy tissue.

It has been found that microwave hyperthermia when used in conjunction with either radiotherapy or with chemotherapy provides more consistent success than either alone. A course of treatment may include several radiotherapy treatments each week, interspersed with microwave hyperthermia treatments. Widespread practical application of such combined therapy depends upon the availability of convenient and predictable microwave hyperthermia methods and apparatus.

U.S. Pat. No. 4,448,198 issued May 15, 1984, to Turner describes an invasive hypertherapy arrangement in which a plurality of microwave applicators are inserted into body tissue. The surgical implantantion requires the use of an expensive operating room and the services of a skilled surgeon, which is not convenient. The applicators provide numerous potential sites for infection and at least require care by the patient. The implanted applicators may interfere with concurrent radiotherapy. Since the dielectric constant of the tumor may differ from that of the surrounding tissue, the energy from the microwave applicators may be partially reflected by the tumor if the applicators are implanted in healthy adjacent tissue, and this may result in an undesirable temperature distribution.

Noninvasive microwave hyperthermia relies upon heating from applicators placed outside the patient's body. This is particularly convenient for small surface tumors, the extent of which can be readily seen. The applicator is often held in contact with the surface being treated to avoid excessive spreading of the energy. For small tumors, a single applicator may be used. The center of the applicator is directed towards the tumor, and the power is applied. Adjacent normal tissue is likely to be at a lower temperature than the temperature at the tumor because a simple applicator such as a horn has a power distribution which decreases away from the center or axis. The temperature of the tumor may be monitored by a small sensor inserted into the tumor. However, if the temperature sensor or probe is electrically conductive it may itself be heated, thereby providing an erroneous indication that the tumor is being heated. Also, the electrically conductive temperature sensor may perturb the field, for example by signal reflection, and may therefore cause constructive interference at a location away from the axis of the application. This may undesirably damage normal tissue. If the probe is thermally conductive it may undesirably cool the tumor.

Large tumors are more difficult to treat. When an applicator such as a horn with a single aperture is used, the power distribution across the aperture of the applicator may heat the center of the area to too high a temperature, and thereby cause burning, or may not heat outlying portions of the tumor to therapeutic temperatures. Failure to sufficiently heat portions of the tumor allows regrowth of the tumor. Burned areas subject to radiation therapy tend to heal slowly or not at all. Ordinarily, radiation therapy is discontinued if the area to be irradiated is injured. Any burning of a part of the tumor by microwave hyperthermia is therefore undesirable, as it may limit therapeutic options. Other variables include surface phenomena such as reduction of surface temperature by perspiration, reflection of microwave energy by bone structures, and the use of heating or cooling pads applied to the surface being treated. A major cause of temperature differences in variation of blood flow to various portions of the tissue being heated. Thus, the treatment of large tumors presents difficulties not found in small tumors.

One known technique for hyperthermia treatment of large tumors is to use a "blanket" applicator which is large enough to cover the entire area to be treated. Such large area applicators are ordinarily made up of an array of a number of relatively small antennas. While such an applicator is theoretically plausible, there are practical difficulties. Since the antennas are spaced one from another on the blanket, those portions of the surface to be treated which lie immediately under an antenna element receive substantially more power than those areas lying between antenna elements and therefore tend to be heated more than outlying areas. Attempts to improve the power distribution by phasing the antennas (as in the Turner patent) to provide constructive reinforcement of the hyperthermia energy at points between antenna elements often fail. The failure comes about because the effective path length of the hyperthermia power passing through a dielectric medium depends upon the dielectric constant of the medium. When the medium is tissue, the dielectric constant varies from point to point and also depends upon the type of tissue (fat, muscle, etc.) through which the field passes. This results in a relatively random distribution of heating, and in the occurrence of hot spots at which burning of the tissue may occur, and also in cold spots at which therapeutic temperatures are not obtained. Such burns may not be visible and may undesirably remain unhealed for long periods if concurrent radiotherapy takes place.

An applicator for providing a uniform microwave field over a relatively large area is described in U.S. Pat. No. 4,271,848 issued June 9, 1981, to Turner. Ideally, such a field should provide uniform heating of a region of tissue. The heating effect will not be uniform, however, because of differences in the amount of absorption of power from the field by various different types of tissue. Even assuming that the heating attributable to the applicator is uniform over the surface to be treated, therapeutic results are not likely to be optimum, because of differences in the vascularization (number and size of blood vessels) and blood flow of various portions of the tissue of surface being heated. A plentiful supply of blood vessels and plentiful supply of blood to one portion of the tissue may result in much lower equilibrium temperatures during hyperthermia than an adjacent area with a paucity of blood vessels and poor supply of blood. Thus, the combination of uneven heating of the tissue by the applicator and of variable amount of cooling by the blood supply results in widely varying temperatures across the surface or throughout the tissues being treated.

A method for treating large tumors is described in U.S. Pat. No. 4,397,314 issued Aug. 9, 1983, to Vaguine. This technique implants temperature sensors in the tumor and in the surrounding tissue. A microwave generator under control of the temperature sensors is coupled to a plurality of external applicators and controls the energy applied to each applicator to provide therapeutic temperatures inside the tumor with an overriding protection of the surrounding healthy tissue. Individual microwave applicators are evaluated during the hyperthermia treatment to determine their effect on the overall heating pattern for optimizing the heating pattern. Besides being invasive, this arrangement has the disadvantage that implanted temperature sensors may have to be moved during the course of the treatment as the tumor size is reduced and healthy tissue replaces it. Since the size of the tumor and the physiological condition of the patient change during the course of the therapy, the optimization of the applicators must be done anew during each session of therapy. This is labor-intensive, and the optimization is subject to human error.

SUMMARY OF THE INVENTION

An arrangement for heating includes an antenna including at least one convolution of conductor centered on an axis. The antenna is adapted for receiving electrical power for heating a surface. A noncontacting temperature sensor is centered on the axis of the antenna with its field of view directed along the axis.

DETAILED DESCRIPTION OF THE INVENTION

Figures 1A, 1B:
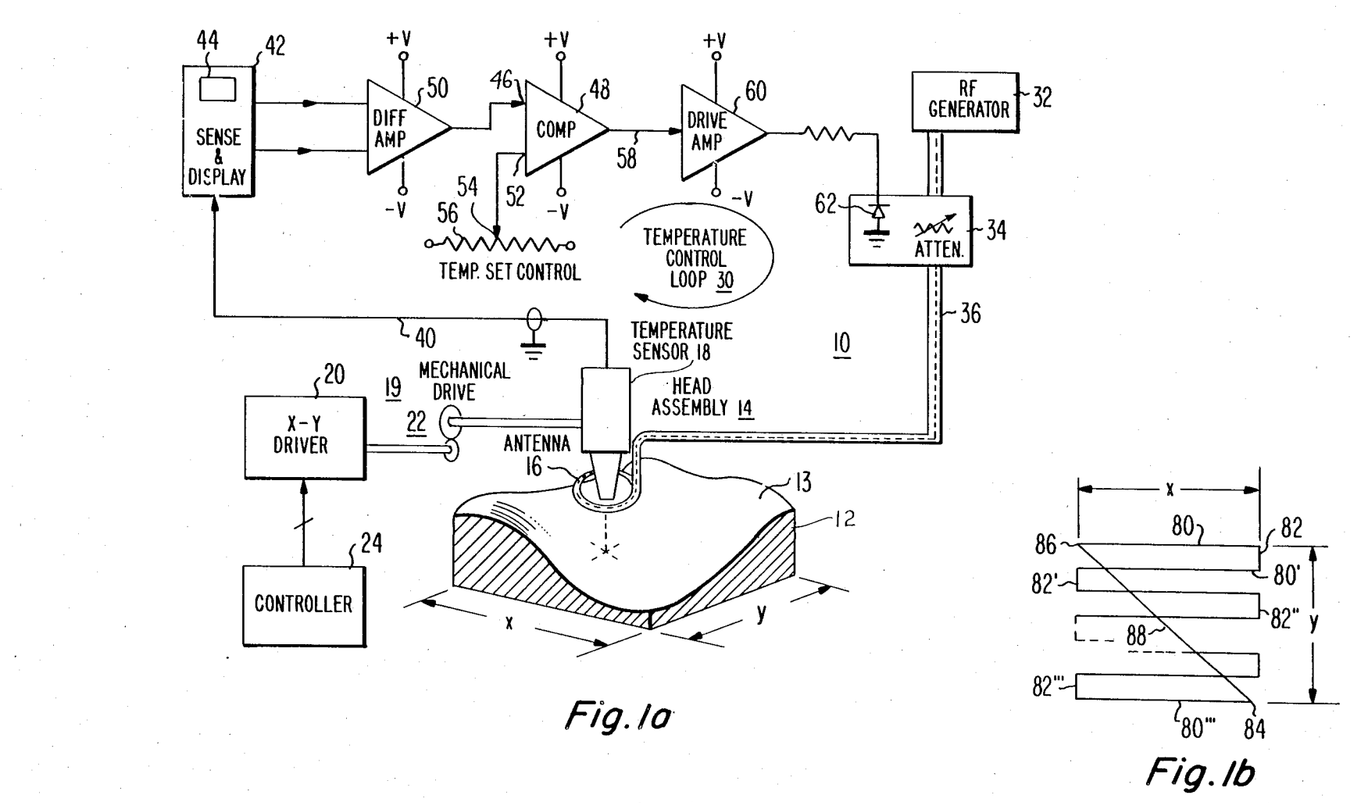
FIG. 1a is a diagram, partially in block and partially in pictorial form, of a hyperthermia apparatus according to the invention.
FIG. 1b illustrates a rectilinear scanning path.

FIG. 1a illustrates an apparatus according to the invention. In FIG. 1a, a portion of tissue to be treated by hyperthermia is designated as 12 and has a skin surface 13. A scanning head assembly designated generally as 14 including an antenna 16 illustrated as a loop and a noncontacting temperature sensor 18 is mechanically scanned over the surface of tissue portion 12 by an X-Y driver 20 and mechanical drive 22 designated together as mechanical scanner 19. The scanning path over which the scanning head assembly 14 is driven is controlled by a controller 24. Within the limits of mechanical drive 22, controller 24 may preselect any portion of the tissue for scanning. As illustrated in FIG. 1a the scanning range is illustrated by dimensions x and y. The rectilinear scanning path is illustrated in FIG. 1b together with the x-y limits established by controller 24. As illustrated, the scanning path includes a plurality of scans 80, 80', ... 80''' separated by steps 82, 82', 82''. .. 82''' for stepping the antenna from one scan position to the next scan position. At the end of scan 80''', the antenna assembly returns from end position 84 to starting position 86 along a path 88, to begin another scan. Thus, antenna assembly 14 is scanned relatively rapidly over the surface in close proximity to, but not touching, the surface being treated.

Antenna 16 and temperature sensor 18 are coupled to a temperature control loop designated generally as 30. Antenna 16 receives power from an electrical signal generator or radio frequency power generator 32 by way of a controllable attenuator 34 and a transmission line 36. The power produced by generator 32 is selected to be great enough to provide more than the required amount of power for hyperthermia treatment of surface tissue portion 12. Attenuator 34 is controlled by temperture sensor 18 in a feedback manner by temperature control loop 30 so as to provide moment-to-moment or instantaneous control of the amount of power flowing from generator 32 to antenna 16 to compensate for variations from point to point in the vasculature of tissue portion 12 and for variations in the absorption of energy from the antenna field by the various types of tissue which may be encountered in tissue portion 12. As mentioned above, such variations from point to point in the absorption and in the amount of cooling would prevent a uniform temperature in tissue portion 12 if the amount of electrical power applied from point to point were uniform.

Feedback loop 30 includes noncontacting temperature sensor 18, which produces a signal on conductor 40 representative of the instantaneous temperature of the tissue portion heated by antenna 16. The temperature indicative signal is applied to a temperature sensing and display electronics illustrated as a block 42 which includes a readout 44 for displaying the indicated temperature. Sensing and display electronics 42 also produces an output signal which is representative of the temperature sensed by sensor 18 which is applied to an input terminal 46 of a difference amplifier or comparator 48 by way of a differential amplifier 50. Comparator 48 compares the signal applied to input terminal 46 with a reference signal applied to input terminal 52 which represents the temperature to which the surface tissue portion 12 is to be raised. As illustrated, the desired temperature setting is derived from a tap 54 on a potentiometer 56 coupled to an appropriate power supply (not illustrated). Comparator 48 produces a control signal on a conductor 58 which is applied to an attenuator drive amplifier 60 for driving the active portion, illustrated as a PIN diode 62, of attenuator 34. PIN diode attenuators are known in the art. Temperature control loop 30 variably attenuates or reduces the amount of power flowing from generator 32 to antenna 16 moment by moment during the scanning of head assembly 14 over tissue portion 12 in order to maintain the desired temperature.

In a particular embodiment of the invention, the mechanical scanner 19 is a commercially available Hewlett-Packard Model 9872A x-y plotter. This computer-controlled mechanical arm 19 can move the assembly 14 to any location within a 28×40 cm rectangular field. This plotter is compatible with a Model 85 Hewlett-Packard computer, also commercially available, and the combination is capable of large numbers of predetermined motions, one of which is illustrated FIG. 1b.

In one embodiment of the invention, temperature sensor 18 is the sensing head of a model C-600M biotherm noncontacting infrared thermometer manufactured by Linear Laboratories, a Division of Linear Corporation, 445 South San Antonio Road, Los Altos, Calif. 94022. This instrument has a temperature range of 10° to 50° C., a sensitivity of 0.1° C. and an accuracy of 0.5° C. The target size is 0.25" (0.6 cm) at 0.75" (1.9 cm). The infrared sensor used in the C-600M is optically filtered to limit the response of the instrument to the infrared spectral band from 8 to 14 microns. This head senses temperature at and near the surface 13 of tissue portion 12 with a speed of response of less than 1 second. The circuit portions 42 of the C-600M produce an output signal which changes one millivolt per degree centigrade of indicated temperature. Because of the fast response of the temperature sensor and of the remainder of control loop 30, relatively uniform temperatures are achieved in the tissue being treated.

Figure 2:
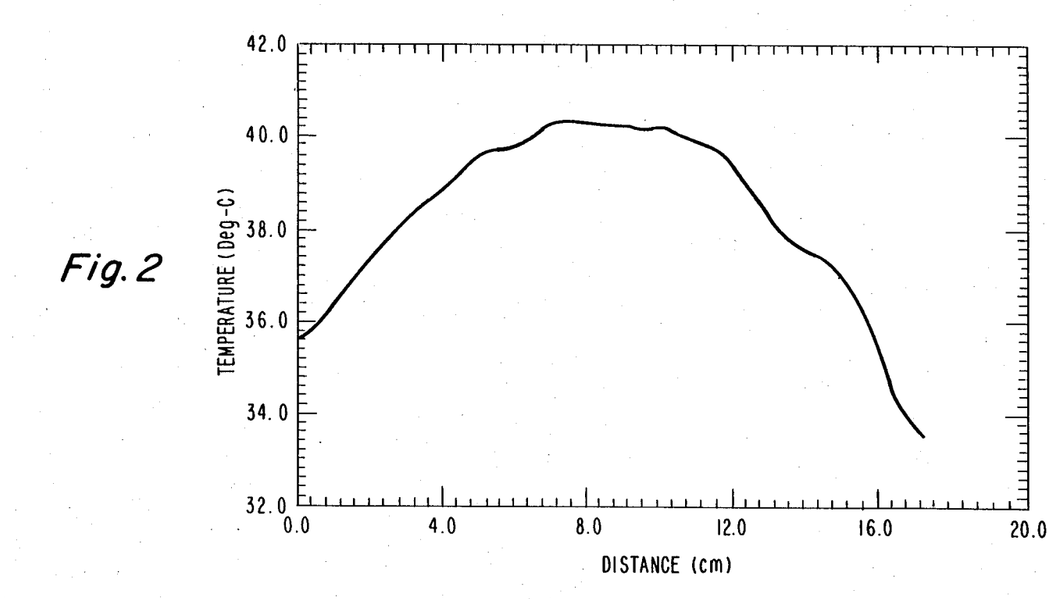
FIG. 2 is a plot of surface temperature versus position along a path over the surface of part of the thigh muscle of a dog after hyperthermia performed according to the invention.

In a particular embodiment of the invention, generator 32 operated at a frequency of 2450 megahertz (MHz) with a power of 100 watts. In a particular test, the antenna and temperature sensor assembly 14 was scanned in a pattern as illustrated in FIG. 1b over a rectangular area having an x dimension of 7.62 cm and a y dimension of 7.62 cm, broken into 4 transverse scans 82 each having a length of 19.05 mm. The antenna 16 of head assembly 14 was typically one to two cm above the treatment area. Separate tests were conducted with the apparatus as so far described on the thigh muscle of a dog and on a muscle equivalent phantom consisting of 68% $H_2O$, 30% gelatin, 1% NaCl, and 1% Formalin. The time required for one complete scan over the area being treated was 11 seconds. After heating was completed by recurrent scans, surface temperatures were measured with the infrared sensor in steps at points separated by 6.35 mm along an x scan lying in the center of the area treated. A maximum temperature rise of 7.8° C. uniform to within ±0.25° C. was obtained on the muscle equivalent phantom over a length of 4.2 cm of the center of the x scan. FIG. 2 is a plot of the surface temperature along a centered x scan after the heating of the thigh muscle of a dog. The temperature is within ±0.1° C. over a length of 4.4 cm.

Figure 3:
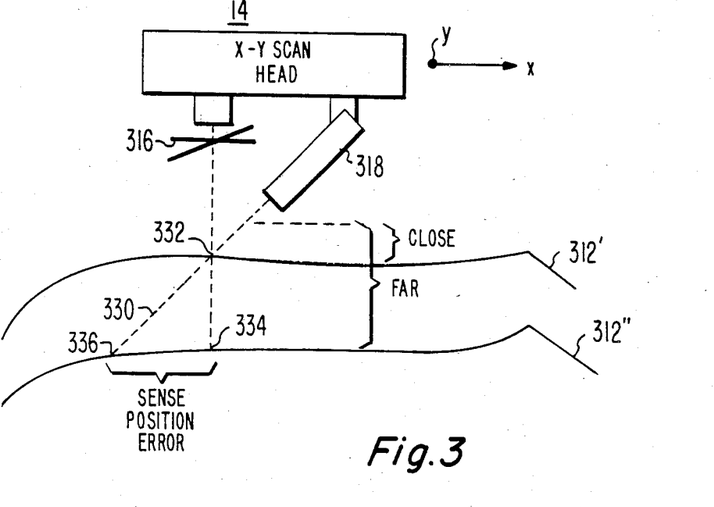
FIG. 3 illustrates a source of error in temperature sensing.

FIG. 3 illustrates a problem which can occur when performing an x-y scan as described in conjunction with FIG. 1a when the antenna, (illustrated as a crossed dipole 316) is offset from the field of view axis 330 of the temperature sensor, illustrated as 318. Tissue portion 312 is illustrated in two positions, a close position 312' and a relatively remote position 312". When axis 330 of the field of view of temperature sensor 318 intersects surface 312' relatively close to antenna 316, surface 312' receives maximum heating from antenna 316 at a position 332 on surface 312'. Position 332 corresponds with the position being viewed or monitored by temperature sensor 318, and therefore the feedback control of temperature will attempt to control the temperature at point 332 to the desired temperature. When tissue portion 312 is in position 312" somewhat more distant from antenna 316, the point on surface 13 receiving the maximum amount of power from antenna 316 corresponds to point 334 on surface 312". The position being viewed by sensor 318, however, is position 336 at the intersection of axis 330 and surface 312". This position does not correspond to the position receiving the maximum amount of energy, so the feedback loop will attempt to control the power applied to antenna 316 in order to maintain point 336 at the desired temperature. This will result in points corresponding to 334 being raised to excessively high temperature. This is undesirable, for reasons described above.

Figure 4:
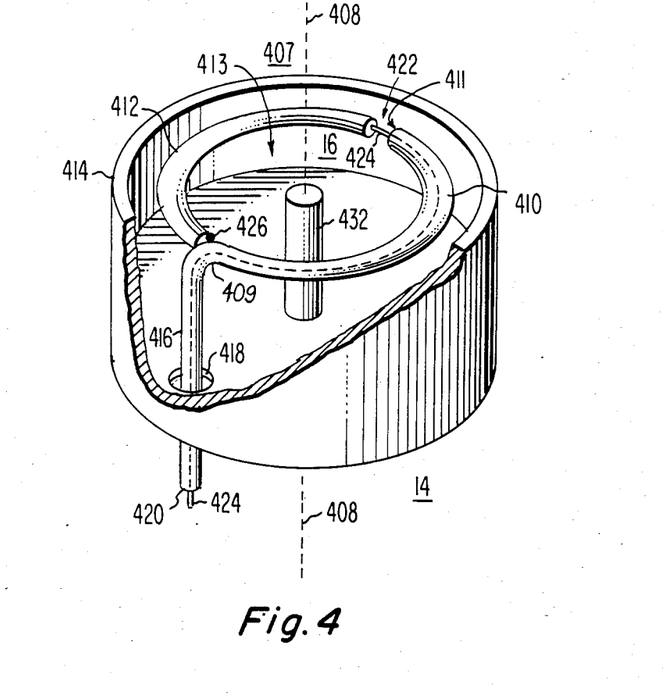
FIG. 4 is a simplified isometric view of the antenna and temperature sensor assembly illustrated in FIG. 1, partially cut away to illustrate the interior.

FIG. 4 illustrates in simplified form the arrangement of the antenna 16 and temperature sensor 18 in scanning head assembly 14. Basically, antenna 16 consists of a loop or convolution designated 407 formed by a first elongated conductive element 410 formed into a semicircle and a second elongated conductive semicircular element 412 formed into a complementary semicircle, with a small gap therebetween in a feed region gap designated generally as 422. Such loop antennas are well known in the art. Major differences among various loop antennas include the method of applying feed signal across feed point or gap 422 for energizing the loop, and in the method for supporting the loop. As illustrated in FIG. 4, a cavity 413 is defined by a conductive housing 414 and a loop 407 is supported at the opening of cavity 413 by a portion 416 of rigid coaxial cable (coax) having an outer conductor 420 and a center conductor 424. Coax portion 416 passes through and is, in turn, supported at an aperture 418 in the closed end of cavity 413. In order to feed signals to feed gap 422 of loop 407, conductive semicircular element 410 is formed as the outer conductor of an extension of coax portion 416, extending from a right angle bend at a location 409 to feed gap 422. In order to clearly differentiate the conductive outer portion of the outer conductor from the coaxial transmission line within portion 410, the coaxial portion within conductive loop portion 410 is designated 411. Coaxial cable portion 416 receives the hyperthermia electrical signals at its input end 420 and couples them past bend 409 and through the interior portion 411 of semicircular coaxial element 410 to loop feed gap 422. At feed gap 422 loop portion 410 ends, and its inner coaxial portion 411 also ends. The center conductor 424 of coax portion 411 passes across gap 422 and connects to solid semicircular conductive loop 412. This arrangement drives the conductive elements 410 and 412 near feed point 422 with mutually out-of-phase signals. The end of semicircular loop portion 412 remote from feed gap 422 is electrically connected to the outer conductor 420 of coaxial element 416 at bend 409 as by a solder connection illustrated as 426. This creates planar conductive loop 407 including conductive portions 410 and 412, interrupted only by gap 422.

When the dimensions of loop antenna 16 are relatively small by comparison with a wavelength at the frequency of the applied electrical signal, the mutually out-of-phase drive signals at feed gap 422 create currents around the loop which are in the same circumferential direction and relatively uniform in their magnitude. Under these conditions, the magnetic fields are directed generally in the direction of axis 408 in the region within loop 16. Variations in magnetic flux due to the loop drive signal do not cause a magnetic flux which crosses (is at right angles to) the length of portion 432 of probe sensor 18. The variation of magnetic flux causes a variation of intensity of that portion of the magnetic field coaxial with probe portion 432, which produces relatively little interaction between the probe and the magnetic field. Because of the low impedance of the relatively short loop, the electric field intensity is relatively low and tends to cancel near central axis 408. Thus, the theorical field intensity on axis 408 is low, and the field distribution is not perturbed by introduction of a metallic object such as a portion 432 of remote temperature sensing element 18. The field of view of temperature sensor 18 coincides with axis 408.

Because the currents around the loop are equal in magnitude, as mentioned above, the current on half-loop 410 equals the current on half-loop 412. Consequently, at bend 409, the current leaving portion 410 equals the current entering portion 412. There is no current difference which can flow on the outside of the outer conductor 420 of coax 416, and coax 416 is therefore electrically invisible.

Figure 5:
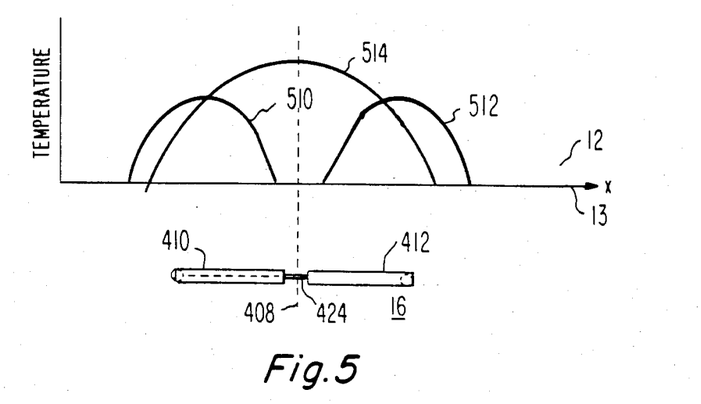
FIG. 5 is a plot of field distribution and heating for an antenna such as that illustrated in FIG. 4.

FIG. 5 illustrates as lobes 510 and 512 the heating or temperature variations which might be expected at surface 13 of tissue portion 12 along a line passing directly under antenna 16 due to the fields near conductors 410 and 412 of loop 407. Thus, one might expect that a loop antenna such as 16 would not provide as much heating in the tissue portion centered on axis 408 directly under the antenna as at points directly under the conductive loop elements. However, in practice the heating effect appears to be a single lobe such as lobe 514 centered on antenna axis 408.

Figure 6A:
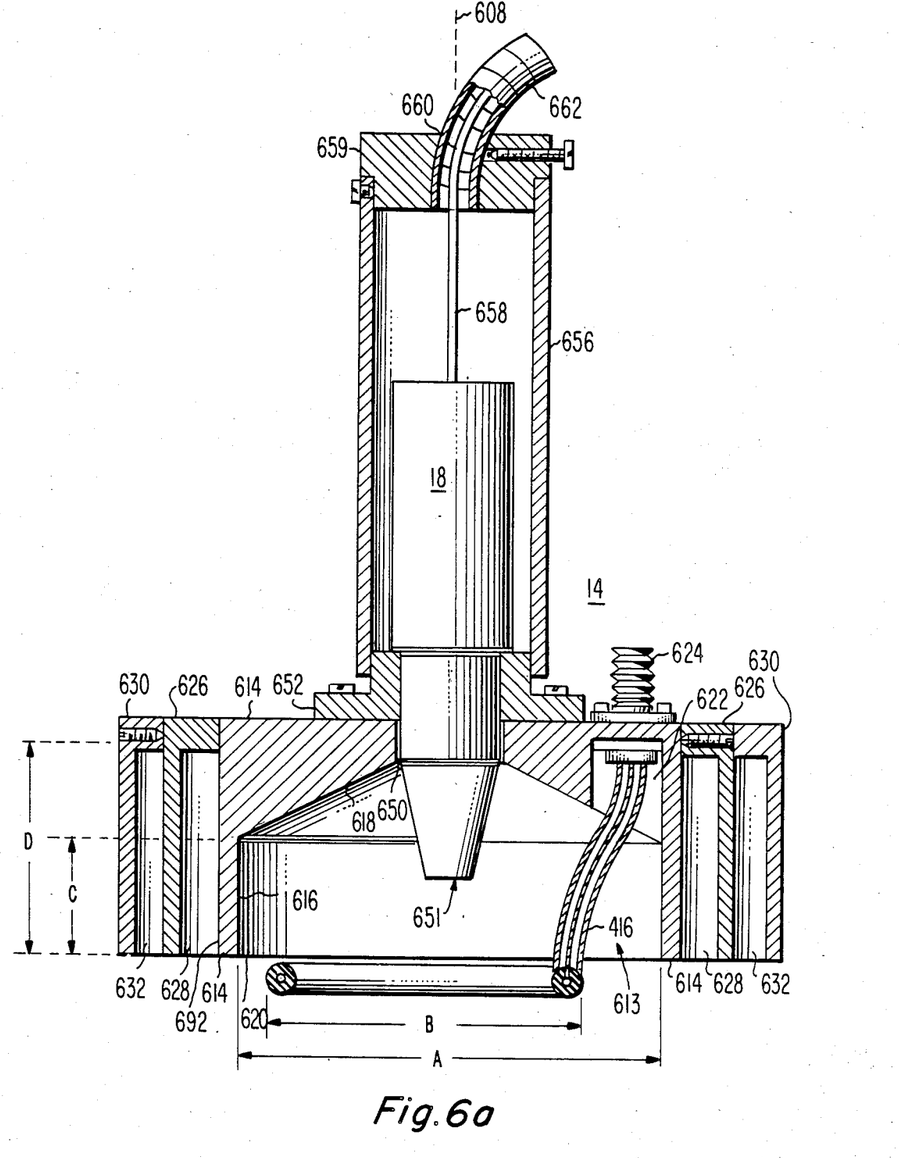
FIGS. 6a,b and c are more detailed cross-sectional, end and exploded views of the assembly of FIG. 4.
Figure 6B:
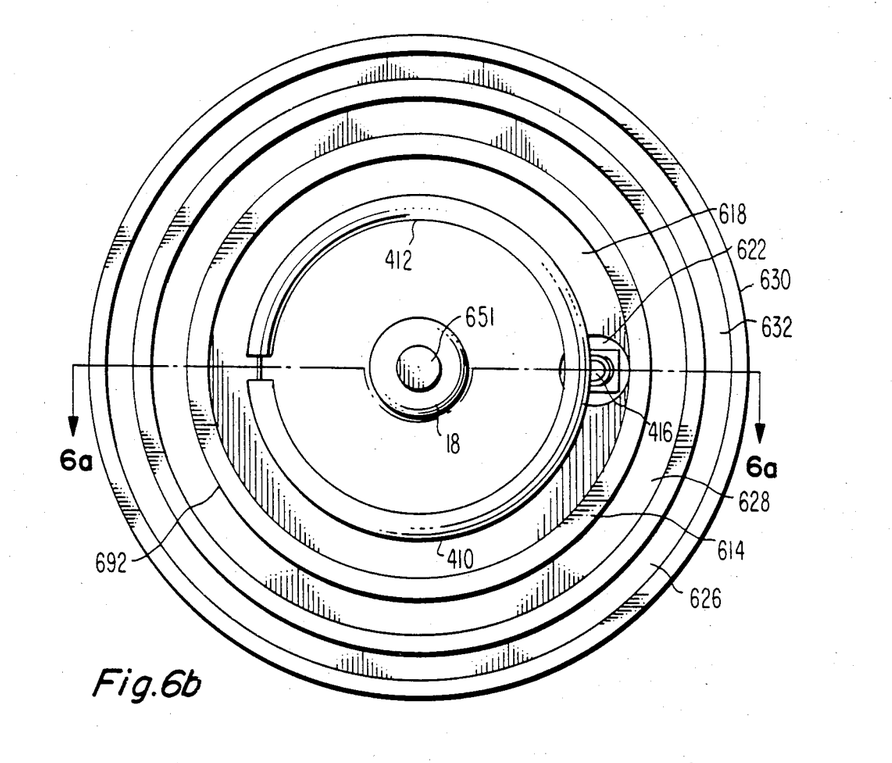
Figure 6C:
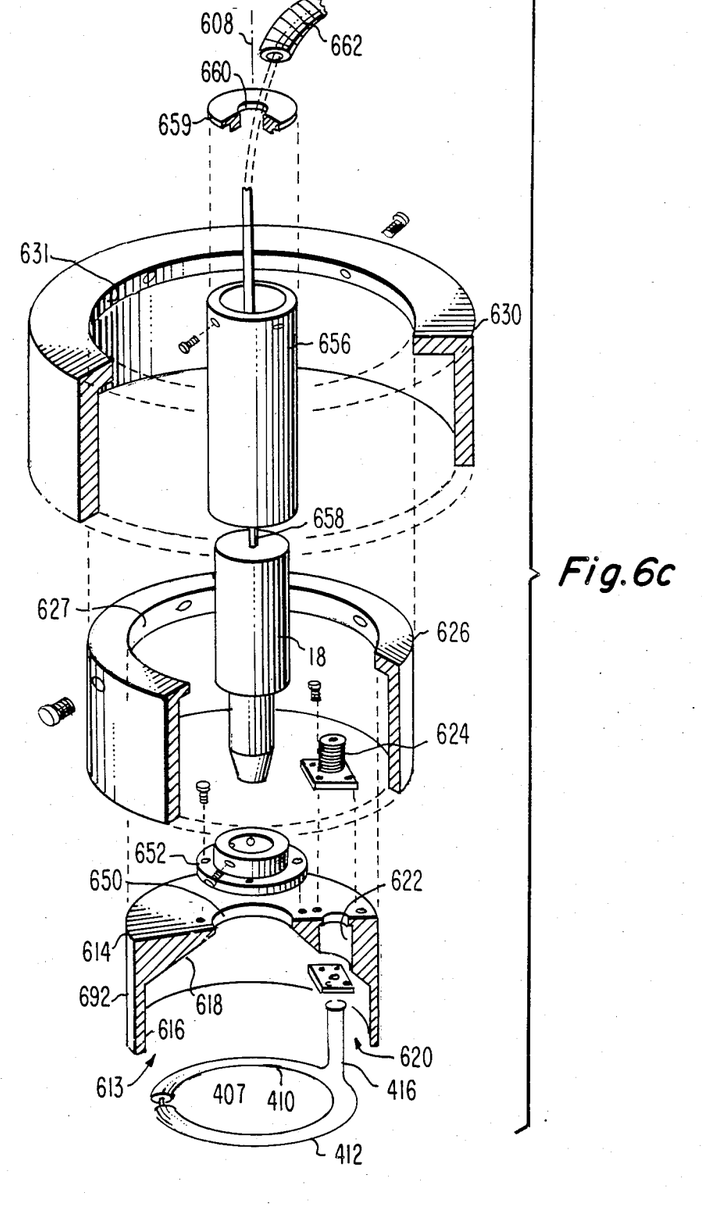

FIG. 6a illustrates in cross-sectional elevation view details of the antenna 16 and temperature sensor 18 of head assembly 14. FIG. 6b is an end view of the structure looking into the side facing the tissue being heated, and FIG. 6c is an exploded view. In FIGS. 6a, b and c a conductive cavity designated generally as 613 is defined by a housing 614 which includes a straight sided figure of revolution portion 616 and a tapered figure of revolution portion 618. Portions 410 and 412 of the loop antenna are located just outside the aperture 620 of the cavity. Coaxial conductor 416 supports the loop antenna including portions 410 and 412. Coax 416 passes into a hole 622 drilled part way through tapered portion 618 of housing 614 and is attached in known fashion to a bulkhead connector 624 which couples the hyperthermia signal from the outside of housing 614 to feed coax 416. Connector 624 provides electrical access to the loop antenna from the side of housing 614 facing away from the patient. During scanning operation, connector 624 is connected to flexible coax cable 36 (FIG. 1). A first conductive annular ring 626 defines an opening 628 which fits tightly around the outer edge of housing 614 and together with outer surface 692 of housing 614 forms an annular radio frequency (RF) choke defined by an annular cavity designated 628 which reduces leakage of energy from the antenna 16 and cavity 613 in directions other than towards the patient. A similar but larger annular ring 630 defines an opening 631 which fits tightly around the outer periphery of ring 626 and forms a second RF choke defined by an annular cavity designated 632 for further reduction of lateral energy leakage. The lengths of cavities 628 and 632 in a direction parallel to axis 608 are selected as known in the art to be approximately one quarter wavelength at the frequency of the electrical hyperthermia signal. As illustrated, cavity housing 614 defines a circular central aperture 650 through which the temperature sensing head or probe 18 of the aforementioned C-600M noncontacting infrared thermometer can protrude, with an aperture 651 in the end of probe 18 for the entry of temperature-representative radiation facing through the center of loop 407. A flange 652 affixed to the rear of cavity housing 614 clamps sensing head 18 firmly in place and provides electrical contact to the metallic portions of sensing head 18 to prevent leakage of residual electromagnetic signal through aperture 650. A support tube 656 is firmly clamped around flange 652 to support head assembly 14 and also to provide protection for sensing head 18. The temperature signals produced by sensing head 18 are conducted by a conductor set 658 to electronics 42 (not illustrated in FIGS. 6a, b or c). The upper part of support tube 656 is closed by a second flange 659 which includes a central aperture 660 for receiving a protective tube 662. Tube 662 is a conductive flexible tube such as flexible conduit (well known as the outer metallic sleeve of common BX house wiring cable for example). Inside the tube 662 is a rubber tube (not illustrated in FIG. 6) through which conductor set 658 passes. The rubber tube provides protection against pinching of conductor set 658 by flexing of the sections of flexible tube 662 during scanning. In normal operation, tube 656 is clamped to the movable arm portion of the x-y plotter by means of a clamping arrangement (not illustrated). The previously mentioned flexible coaxial cable 36 is coupled to coaxial connector 624 to provide power to antenna 16 from attenuator 34, and conductor set 658 is coupled to electronics 42 to provide temperature sensing for control of the power, all as described in conjunction with FIG. 1.

In the particular embodiment of the invention producing the results described in conjunction with FIG. 2, coax 416 and elements 410 and 412 of loop antenna 16 are formed from 0.141 (3.58 mm) "semi-rigid" coaxial transmission line. For operation at 2450 megahertz, cavity diameter A is 3.450" (8.76 cm), loop dimension B is approximately 1.35" (3.43 cm), cavity dimension C is 0.984" (2.49 cm), and choke depth D is 1.204" (3.06 cm).

Figure 7:
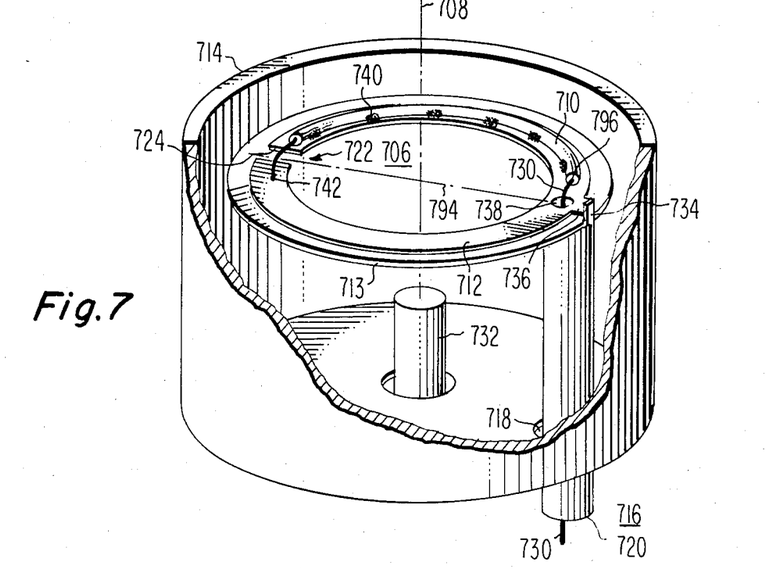
FIG. 7 is an isometric view of a simplified antenna according to another embodiment of the invention, partially cut away to reveal interior details.

FIG. 7 illustrates in simplified isometric view another embodiment of a loop antenna and temperature sensor assembly in accordance with the invention. In FIG. 7, a cavity-defining conductive housing 714 is cut away to reveal a disc shaped printed circuit board designated generally as 706 centered on an axis 708 and including a single convolution or loop of conductive material 712 such as copper printed on a dielectric substrate material 713. Loop 712 is broken at a feed gap 722. Printed circuit board 706 is held in position coaxial with portion 732 of temperature probe 18 and near the aperture of the cavity defined by housing 714. Printed circuit board 706 is supported by the outer conductor 720 of a rigid coaxial cable designated generally as 716 passing through an aperture 718 in the bottom of housing 714. The lower or cavity-facing surface of printed circuit board 706 substrate 713 is epoxied to the top of outer conductor 720 of coax 716 to provide support. A tab 734 which is part of outer conductor 720 protrudes above the level of printed circuit board 706 at a point near the periphery of printed circuit board 706 lying on a line 794 passing diametrically through gap 722 and axis 708. A conductive extension 736 of conductive loop 712 centered on line 794 extends along the top surface of printed circuit board 706 towards tab 734 and is soldered thereto to provide electrical continuity between outer conductor 716 and a point on conductive loop 712 diametrically opposite feed gap 722. A center conductor 730 of coax section 716 extends from the top portion of coax section 716 and through an aperture 738 formed in substrate 713 and in conductive loop 712 and centered on line 794, and is electrically isolated from conductive loop 712 in the region diametrically opposite feed point 722. Center conductor 730 thus passes in electrically isolated fashion through aperture 738, and is connected at a point 796 to the center conductor of a section 710 of miniature coax which extends from a point on conductive loop 712 near tab 734 halfway around conductive portion 712 to a point near feed gap 722, with its outer conductor soldered to the upper portion of conductor 712 at various points such as 740 along its length. The end of coax section 710 remote from tab 734 ends at feed gap 722 with its outer conductor in electrical contact with conductor 712 and terminated at one side of the gap, and with its center conductor 724 extending across the gap to contact conductor 712 at a point 742. In effect, coax section 710 is a continuation of coax 716, so the configuration is electrically equivalent of the arrangement of FIG. 4. However, the arrangement of FIG. 7 has the advantage that the characterizing dimensions of the loop are established by the printed circuit pattern of conductor 712 of printed circuit board 706. This is especially advantageous when high frequency antennas are to be manufactured because of the close control over tolerances provided by the printed circuit manufacturing technique.

Figure 8:
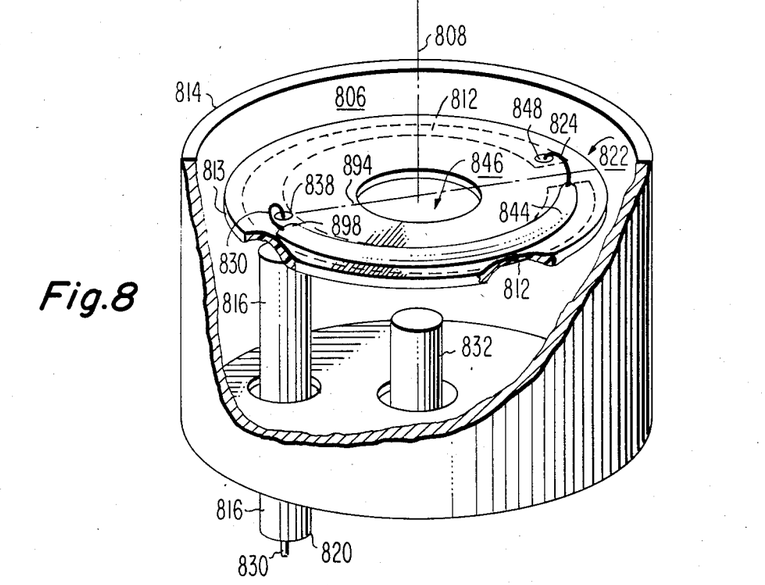
FIGS. 8, 9a and 9b are isometric views of simplified antenna according to other embodiments of the invention, partially cut away to reveal interior details.
Figure 9A:
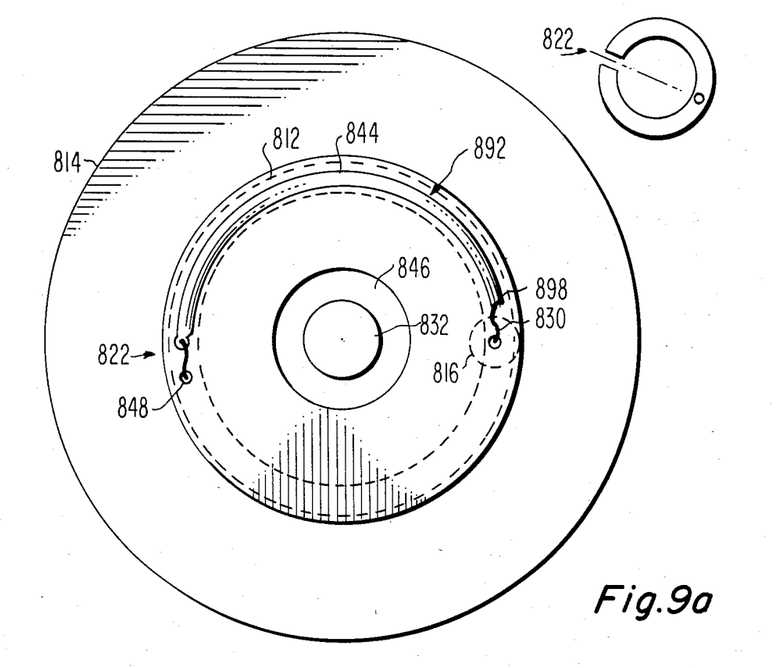
Figure 9B:
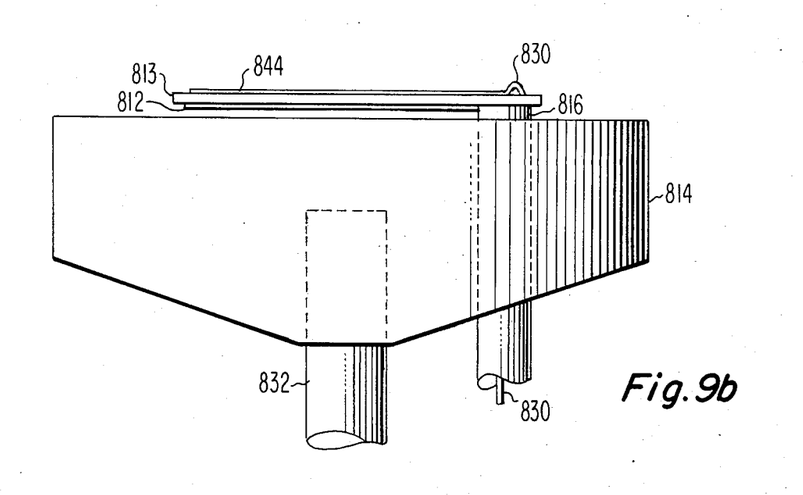

FIG. 8 is a simplified isometric view, partially cut away, of another antenna which uses a printed circuit board for definition, and FIGS. 9a and 9b are top and side views, respectively, of the antenna of FIG. 8 showing the shape of the cavity more clearly. The cavity and temperature probe are the same as in FIGS. 4 and 7 and are not further discussed. The antenna illustrated in FIGS. 8, 9a and 9b includes a single convolution or turn loop antenna including a loop conductor 812 defining a feed gap 822 printed on the bottom (cavity-facing) side of the substrate 813 of a printed circuit board 806. Printed circuit board 806 defines a large axial aperture 846 by which portion 832 of temperature sensor 18 may view the tissue being heated, without attenuation of temperature representative radiation by passage of the radiation through the body of printed circuit substrate material 813. Printed circuit board 806 also defines an aperture 838 lying on a line 894 passing diametrically through axis 808 and feed gap 822. Center conductor 830 of a supporting coaxial transmission line 816 can pass to the upper side of printed circuit board 806 through aperture 838 in order to make connections. Since printed circuit loop 812 is on the bottom or cavity facing side of printed circuit substrate material 813, it can be soldered directly to outer conductor 820 of coax 816 without the need for a tab as described in conjunction with FIG. 7. Instead of a coaxial transmission line 710 soldered to the loop conductor as illustrated in conjunction with FIG. 7 to carry feed energy to the feed point, the arrangement of FIGS. 8, 9a and 9b includes a microstrip transmission line 892 formed by an elongated, narrow strip conductive portion 844 printed on the upper side of printed circuit insulating substrate 813 and extending from a point near feed gap 822 to a point 898 near aperture 838 along a path centered over a portion of conductive loop 812. Conductive portion 844 coacts with that broad conductive portion of conductive loop 812 which it overlies to form microstrip transmission line 892. The center conductor 830 of supporting coax 816 passes in insulated manner through aperture 838 and is soldered to conductive portion 844 at point 898. Microstrip transmission line 892 carries hyperthermia signal applied at point 898 from coax 816 to feed gap 822. At the feed gap, a jumper wire 824 is soldered to the end of conductor portion 844. Wire 824 crosses the gap and is soldered to a conductive eyelet 848 which passes through the insulating material 813 and makes contact with loop conductor 812. Those skilled in the art will understand that the arrangement illustrated in FIGS. 8, 9a and 9b corresponds to the arrangement illustrated in FIG. 7 with microstrip transmission line 892 being substituted for coaxial transmission line 710, and with an additional hole or aperture 846 to prevent attenuation of the temperature indicative radiation.

Figure 10A:
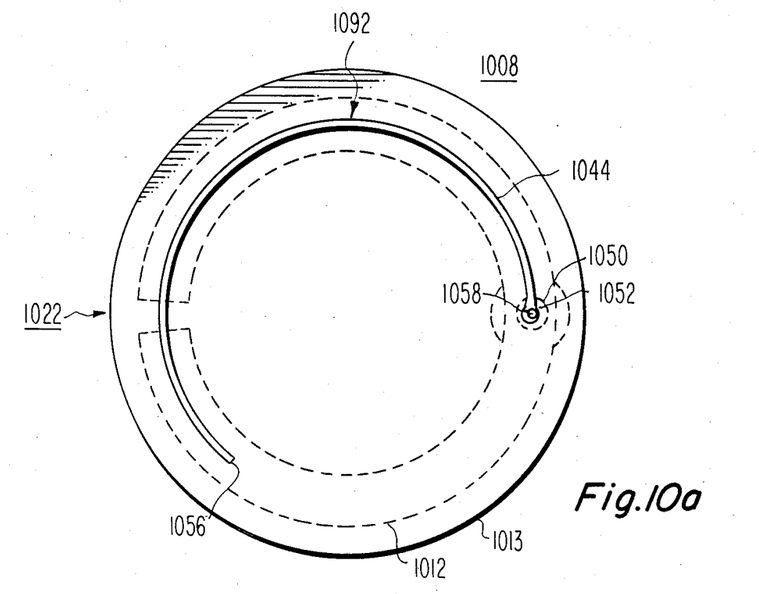
FIGS. 10a and 10b are top and bottom views, respectively, of the printed circuit board of an antenna according to an embodiment of the invention which provides capacitance tuning of the loop antenna.
Figure 10B:
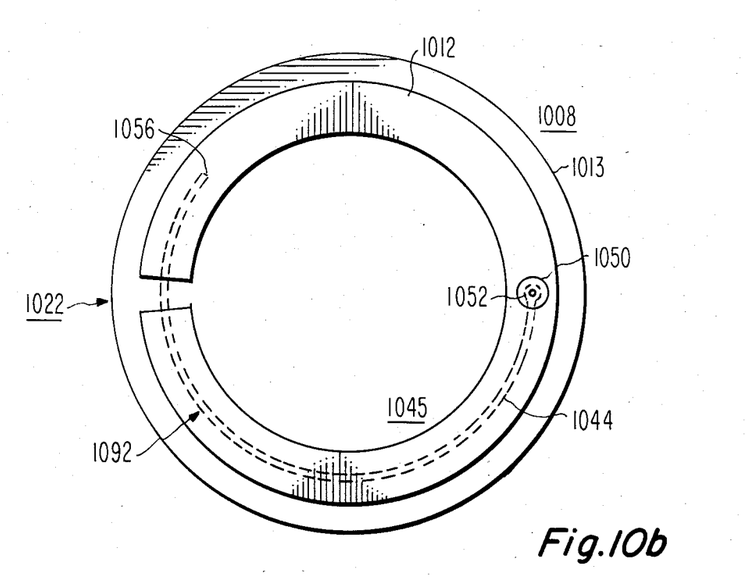

FIG. 10a illustrates the top side of a circuit board 1008 of an antenna according to another embodiment of the invention, and FIG. 10b illustrates the bottom (cavity-facing) side of the same board. The associated cavity, supports and temperature sensor are not illustrated. In FIG. 10, printed circuit board 1008 includes a substrate 1013 on which is printed a convolution 1012 of conductor defining a feed gap 1022 and also defining a circular portion 1050 without conductor which is located diametrically opposite feed gap 1022. Located on the top side of printed circuit board 1013 is a portion of elongated printed conductor 1044 defining a loop coacting with that portion of conductor 1012 which it overlies to define a microstrip line designated generally as 1092. The microstrip line starts at an enlarged portion 1052 and extends over a portion of loop conductor 1012 past gap 1022 to end at point 1056. Enlarged portion 1052 of conductor 1044 has an aperture 1058 in its center and forms a bonding pad to which the center conductor of a supporting coax line (not illustrated in FIGS. 10a, b) may be connected. This arrangement substantially corresponds to the arrangement illustrated in FIGS. 8 and 9, except that the portion of conductor 1044 extending between gap 1022 and point 1056 is in effect a capacitance in series with conductive loop 1012. The value of the capacitance is selected by adjustment of position 1056 to provide tuning of the inductance of the loop antenna formed by conductor 1012.

Figures 11, 11A, 11B, 11C, 11D:
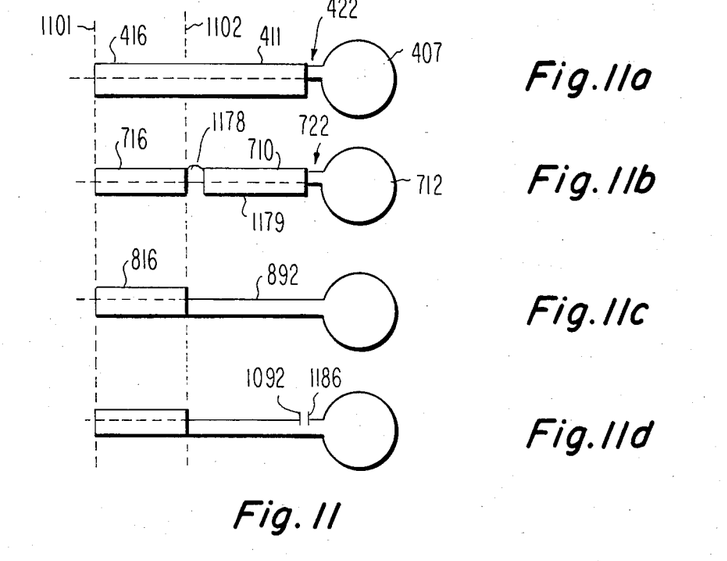
FIGS. 11a, 11b, 11c and 11d are simplified schematic diagrams of the antennas of FIGS. 7, 8, 9 and 10.

The differences between the arrangements of FIGS. 4, 7, 8, and 9 are illustrated in the schematic diagrams of FIGS. 11a–11d. In FIG. 11a, dotted line 1101 represents an electrical plane corresponding to the bottom of the cavity, and dotted line 1102 represents the plane of the radiating loop. In FIG. 11a, coax portion 416 couples signal from the plane of the cavity to the plane of the loop and directly through second coaxial portion 411 to feed loop 407 directly. The arrangement of FIG. 11b corresponds with the arrangement of FIG. 7. In FIG. 11b support coax 716 connects to coax section 710 by jumpers 1178 representing the junction between coax 716 and coax section 710 of FIG. 7. The arrangement of FIG. 11c corresponds to that of FIG. 8, with coax section 816 feeding microstrip line 892. The arrangement of FIG. 11d represents the arrangement of an antenna according to FIG. 10, in which the capacitance between conductor 1044 and conductive strip 1012 in the region between gap 1022 and the point 1056 is represented as a capacitor 1186.

Figure 12:
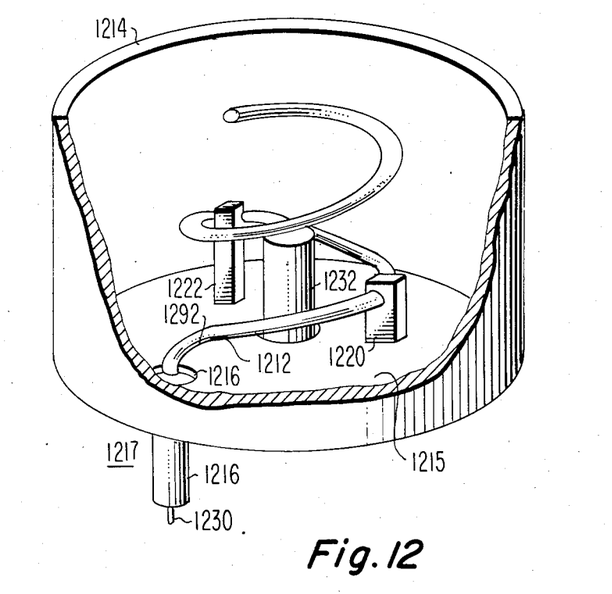
FIG. 12 is an isometric view of a simplified arrangement according to an embodiment of the invention with the cavity partially cut away to show details of a single conductor multiconvolution antenna.

FIG. 12 illustrates in simplified isometric view a nonplanar single-conductor antenna according to the invention including a cavity defined by a conductive housing 1214 which is cut away to illustrate a junction of the outer conductor 1216 of a feed coax 1217 with the bottom of housing 1214. Center conductor 1230 of feed coax 1217 is electrically isolated from housing 1214 and connects at a point 1292 to the bottom of a multiturn multi-convolution conductor 1212 which is supported by blocks 1220 and 1222 of insulating material. Blocks 1220 and 1222 are fastened to the bottom wall 1215 of cavity 1214. As illustrated, conductor 1212 is substantially self-supporting and makes approximately one and three-quarter turns. As known, such an arrangement defines a helical antenna which has well-defined properties among which are higher gain than that of a single convolution loop antenna.

Figure 13A:
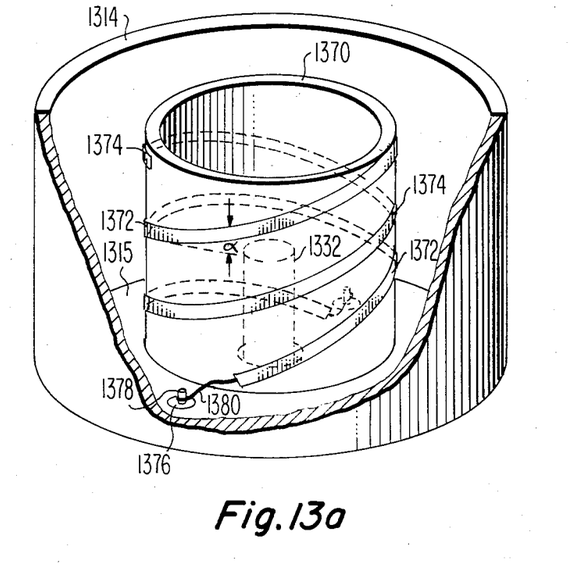
FIG. 13a is an isometric view of an assembly with the cavity partially cut away to show details of a simplified multiconductor multi convolution antenna according to another embodiment of the invention.
Figure 13B:
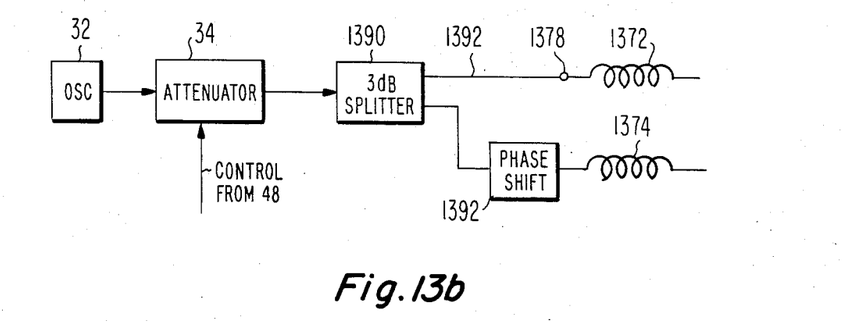
FIG. 13b is a functional block diagram of a drive arrangement for the conductors of the antenna.

FIG. 13a illustrates a multi-convolution multiconductor nonplanar antenna. In FIG. 13a, 1314 is a cavity-defining conductive housing. Within the cavity defined by 1314 is a cylinder 1370 of insulating material such as glass-impregnated epoxy. Printed on the outer surface of cylinder 1370 are a pair of conductors 1372 and 1374. Conductors 1372 and 1374 are helically arranged on cylinder 1370 with the same pitch angle $\alpha$ and are physically disposed at positions 180° apart on cylinder 1370. The helical conductors 1372 and 1374 are insulated from each other and from housing 1314. Arranged at diametrically opposite positions on the bottom of the cavity defined by housing 1314 are a pair of coaxial feeds, one of which is visible in the foreground and is designated 1376. The outer conductors of the coaxial feeds are connected to housing 1314. Center conductor 1378 of coaxial feed 1376 is connected by a jumper wire 1380 to an end of helical conductor 1372. The other coaxial feed is located at a point not visible in FIG. 13a, and feeds the lower end of helical conductor 1374 in a like manner. A portion 1332 of a temperature sensing element is coaxially aligned with the cavity defined by housing 1314 and with the axis of cylinder 1370 on which helical antenna conductors 1372 and 1374 are printed and is illustrated by dotted lines. The antenna defined by helical windings 1372 and 1374 as known radiates axially within certain frequency ranges when the ends nearest bottom 1315 of cavity 1314 are fed in mutually opposite phase. FIG. 13b illustrates in block diagram form an arrangement for driving the helical windings 1372, 1374 in the proper phase. In FIG. 13b, oscillator 32 drives controllable attenuator 34, the control output of which in turn drives a 3 dB power splitter 1390 which divides the signal into equal portions, one of which is applied directly to helical winding 1372 by way of a conductor 1392 and the other of which is applied to helical winding 1374 by a low attenuation phase shifter 1392. Phase shifter 1392 may be a half-wavelength of transmission line.

Other embodiments of the invention will be apparent to those skilled in the art. For example, the convolution of conductor may be square rather than round. Multifilar helicies may as known be used, provided that properly phased drives are provided. Tapered helices may be used to provide broad bandwidth. While the described embodiments make use of a cavity reflector, other types of reflectors may be used. If the antenna has sufficient directivity, no reflector is necessary. Multiturn loops may be planar spirals rather than axially extended helices, and may defined by generating functions which are Archimedean (defined by the product of a constant times an angle) or exponential (defined by an angle raised to a constant power), or may be defined by other functions.

What is claimed is:
1. An apparatus for heating comprising:
an antenna including at least one convolution of conductor having an axis, said antenna being adapted for being placed near a volume to be heated with said axis roughly normal to the surface of said volume, said antenna also being adapted for receiving radio frequency current in said at least one convolution of conductor for transducing the power represented by said current to a radio frequency field, said radio frequency field having a null on said axis in the vicinity of said at least one convolution of conductor;
reflecting and supporting means electromagnetically and mechanically coupled to said at least one convolution of conductor for directing said radio fre- quency field towards said surface and for supporting said at least one convolution of conductor; and temperature signal sensing means mechanically coupled to said reflecting and supporting means for being supported at a position centered on said axis for sensing the temperature of said surface, whereby said temperature signal sensing means is located at a position of low radio frequency field intensity and has little effect on, and is little affected by, said radio frequency field.

2. An apparatus according to claim 1 wherein said at least one convolution of conductor is a single loop of conductor centered on said axis and lying in a plane and definng a gap between ends of said loop.

3. An apparatus according to claim 2 wherein said reflecting and supporting means comprises:
 a reflector including an aperture therein; and
 a rigid coaxial transmission line including an outer conductor and an inner conductor passing through said aperture in said reflector, said outer conductor being mechanically and electrically coupled to said loop on one side of said gap, and said inner conductor being electrically coupled to said loop on the other side of said gap.

4. An apparatus according to claim 2 wherein said single loop of conductor is a pattern of metalization on a printed circuit board.

5. An apparatus according to claim 4 wherein said reflecting and supporting means comprises:
 a reflector including an aperture therein, said aperture being at a distance from said axis equal to the radius of said loop; and
 a coaxial transmission line including an inner conductor and a rigid outer conductor, said transmission line passing through said aperture defined by said reflector and parallel with said axis, said printed circuit board being mechanically coupled to said outer conductor for being supported thereby, and said inner and outer conductors being electrically coupled across said gap.

6. An apparatus according to claim 1 wherein said temperature signal sensing means includes output conductor means, and produces an electrical signal associated with said output conductor means, and said reflecting and supporting means comprises an aperture through which said output conductor means passes.

7. An apparatus according to claim 6 wherein said temperature signal sensing means is a thermopile radiation sensor for producing a direct sense signal and said output conductor means comprises a wire pair for carrying said direct sense signal.

8. An apparatus for producing uniform hyperthermic temperature over a large vasculated tissue portion, comprising:
 an antenna having a directional characteristic for propagating energy generally along an axis of maximum response but having a low field intensity on said axis near said antenna;
 electrical signal generating means coupled to said antenna, the power of said electrical signal generating means being controllable in response to a control signal applied at a control input terminal;
 noncontacting temperature indicator means for generating a temperature signal instantaneously indicative of the temperature of tissue within its field of view;
 controllable mounting and drive means coupled to said antenna and to said temperature indicator means for recurrently scanning said antenna along a predetermined path over said portion of tissue to be heated whereby said tissue is heated in response to an electromagnetic field produced by said antenna in response to said electrical signal, but said tissue may not be uniformly heated because of variations in the vasculature or field absorption by the tissue, or for other reasons, said tempertaure indicator means being located along said axis near said antenna whereby said temperature indicator means lies in a region of low field intensity and does not perturb said antenna and is not perturbed thereby, and said temperature indicator means indicates the temperature of said portion of tissue; and
 comparator means coupled to said temperature indicator means and to said control input terminal of said electrical signal generating means for comparing said temperature signal with a predetermined signal for generating said control signal for instantaneous control of said power for closing a feedback loop for adjusting said power instant by instant during said scanning for maintaining said tissue at a uniform temperature.

9. An apparatus according to claim 8 wherein said predetermined path is a planar rectilinear scanning path.

10. An apparatus according to caim 9 wherein said antenna is directional and is oriented with said axis orthogonal to said planar scanning path and directed towards the surface of said tissue portion.

11. An apparatus according to claim 10 wherein the axis of said field of view of said temperature indicator means is directed parallel to said axis of maximum response.

12. An apparatus according to claim 11 wherein said axis of said field of view of said temperature indicator means coincides with said axis of maximum response.

13. An apparatus according to claim 12 wherein said antenna comprises at least one convolution of conductor having an axis coinciding with said axis of said field of view.

14. An apparatus according to claim 9 wherein said antenna comprises a convolution of conductor centered about said axis of maximum response and lying in a plane parallel with the plane of said scanning.

* * * * *